United States Patent [19]

Sarvazyan

[11] Patent Number: 5,606,971
[45] Date of Patent: Mar. 4, 1997

[54] METHOD AND DEVICE FOR SHEAR WAVE ELASTICITY IMAGING

[75] Inventor: Armen P. Sarvazyan, East Brunswick, N.J.

[73] Assignee: Artann Corporation, a NJ Corp., East Brunswick, N.J.

[21] Appl. No.: 555,851

[22] Filed: Nov. 13, 1995

[51] Int. Cl.$^6$ ........................................ A61B 8/00
[52] U.S. Cl. ........................................ 128/660.02
[58] Field of Search .................. 128/660.01, 660.02, 128/774; 73/597, 602

[56] References Cited

U.S. PATENT DOCUMENTS

| | | | |
|---|---|---|---|
| 4,947,851 | 8/1990 | Sarvazyan et al. | 128/660.02 |
| 5,038,787 | 8/1991 | Antich et al. | 128/660.01 |
| 5,056,357 | 10/1991 | Dymling et al. | |
| 5,099,848 | 3/1992 | Parker et al. | |
| 5,107,837 | 4/1992 | Ophir et al. | |
| 5,115,808 | 5/1992 | Popovic et al. | 128/660.02 |
| 5,143,070 | 9/1992 | Ophir et al. | |
| 5,178,147 | 1/1993 | Ophir et al. | |
| 5,293,870 | 3/1994 | Ophir et al. | |

OTHER PUBLICATIONS

Cespedes I, Ophir J, Ponnekanti H, and Maklad N: Elastography: Elasticity imaging using ultrasound with application to muscle and breast in vivo. Ultrasonic Imaging 1993; 15: 73–81.
Frizzell LA, Carstensen EL, and Dyro JF: Shear properties of mammalian tissues at low megahertz frequencies. J Acoust Soc Am 1976; 60: 1409–1411.
Krouskop TA, Dougherty DR, Levinson SF: A pulsed Doppler ultrasonic system for making non–invasive measurements of the mechanical properties of soft tissue. J Rehabil Res Dev 1987; 24(2): 1–8.
Lerner RM, Huang SR, and Parker KJ: Sonoelasticity images derived from ultrasound signals in mechanically vibrated tissues. Ultrasound in Med & Biol 1990; 16: 231–239.
Lerner RM, Parker KJ, Holen J, Gramiak R, Waag RC: Sono–Elasticity: Medical Elasticity Images Derived from Ultrasound Signals In Mechanically Vibrated Targets. Sono–Elasticity. Acoustical Imaging, vol. 16, Ed. Lawrence W. Kessler, Plenum Press, New York and London 1988, pp. 317–327.
Muthupillai R, Lomas DJ, Rossman PJ, Greenleaf JF, Manduca A, Ehman RL: Magnetic Resonance Elastography by Direct Visualization of Propagating Actoustic Strain Waves, Science 1995, vol. 269, pp. 1854–1857.
O'Donnell M, Skovoroda AR, Shapo BM and Emelianov SY. Internal displacement and strain imaging using ultrasonic speckle tracking. IEEE Transactions on Ultrasonic Ferroelectrics and Frequency Control UFFC 1994; 41: 314–325.
Ogura K, Nishiki M, Banno H. Wide Band Receiving Characteristics of Piezo–Rubber Hydrophone. Japanese Journal of Applied Physics, 1992, 31: Supplement 31–1, 278–280.
Ophir J, Cespedes I, Ponnekanti HL, Yazdi Y, and Li X: Elastography: A quantitative method for imaging the elasticity of biological tissues. Ultrasonic Imaging 1991; 13: 111–117.

(List continued on next page.)

Primary Examiner—George Manuel
Attorney, Agent, or Firm—Mathews, Woodbridge & Collins

[57] ABSTRACT

A method and devices for Shear Wave Elasticity Imaging (SWEI). The method employs a focused ultrasound transducer which remotely induces a shear wave in a tissue by sending modulated ultrasonic pulses. The shear wave of the frequency of the modulating signal is detected. The values of the shear modulus and dynamic shear viscosity of tissue are evaluated from the measured values of velocity and attenuation of shear waves. Several devices for carrying out the method are described. Devices based on the method can be used as a diagnostic tool in the detection of abnormalities in tissue, such as those caused by cancer or other lesions and characterizing processes in tissues accompanied by changes in their mechanical properties.

20 Claims, 3 Drawing Sheets

OTHER PUBLICATIONS

Parker KJ, Huang SR, Musulin RA, Lerner RM: Tissue response to mechanical vibrations for "sonoelasticity imaging". Ultrasound Med Biol 1990; 16(3): 241–246.

Sarvazyan AP, Goukassian D, Maevsky E, Oranskaja G, Skovoroda A, Emelianov S, Klishko A, Mironova G, Sholokhov V, and Ermilova V: Elasticity imaging as a new modality of medical imaging for cancer detection. In Proc of International Workshop "Interaction of Ultrasound with Biological Media", Valenciennes, France, 1994; 69–81.

Sarvazyan AP, Skovoroda AR, Emelianov SY, Fowlkes JB, Pipe JG, Adler RS, Buxton RB, Carson PL: Biophysical Bases of Elasticity Imaging. Acoustical Imaging, vol. 21, Ed. J. P. Jones, Plenum Press, New York, 1995, 223–240.

Starritt HC, Duck FA, and Humphrey VF: An experimental investigation of streaming in pulsed diagnostic ultrasound beams. Ultrasound Med Biol 1989; 15: 363–373.

Sugimoto, T., Ueha, S., Itoh, K. Tissue Hardness Measurement Using The Radiation Force of Focused Ultrasound. IEEE 1990 Ultrasonic Symposium, 1377–80.

Yamakoshi Y, Sato J, Sato T: Ultrasonic imaging of the internal vibration of soft tissue under forced vibration. IEEE Transactions on Ultrasonic Ferroelectrics and Frequency Control 1990: 37, 45–53.

METHOD AND DEVICE FOR SHEAR WAVE ELASTICITY IMAGING

TECHNICAL FIELD

The present invention relates to a method and devices for determining tissue elasticity in various parts of the body and using such information as a diagnostic tool in the detection of abnormalities of tissue, such as those caused by cancer or other lesions and characterizing processes in tissues accompanied by changes in their mechanical properties, such as muscle contraction, development of edema, and so forth. The clinical importance and the diagnostic value of elasticity imaging of tissues are based on the observation that changes in shear elasticity modulus of tissues reach several orders-of-magnitude during pathological and physiological processes in the body.

BACKGROUND OF THE INVENTION

There are a number of methods of elasticity imaging where elasticity of tissues is evaluated using the data on the strain in a tissue subjected to a given stress. In most of these methods, the information about the strain in the tissue is obtained with the use of conventional ultrasonic imaging techniques.

One approach attempts to determine the shear elasticity of tissue by applying a low frequency vibration (e.g. 100 Hz) to the tissue surface while measuring the amplitude and phase of tissue vibration using ultrasound imaging techniques. See e.g., T. A. Krouskop et al., *A Pulsed Doppler Ultrasonic System for Making Non-Invasive Measurement of Mechanical Properties of Soft Tissue*, J. Rehab. Res. Dev. Vol. 24, 1–8 (1987); see also R. M. Lerner et al., "Sonoelasticity" Images Derived from Ultrasound Signals in Mechanically Vibrated Tissues, Ultrasound in Med. & Biol. Vol. 16, No. 3, 231–239 (1990), and K. J. Parker et al., U.S. Pat. No. 5,099,848 (1992), and Y. Yamakoshi et al., *Ultrasonic Imaging of Internal Vibration of Soft Tissue Under Forced Vibration*, IEEE Transactions on Ultrasonics, Ferroelectrics, and Frequency Control, Vol. 7, No. 2, 45–53 (1990).

A method for measuring and imaging tissue elasticity is described in Ophir et al., U.S. Pat. No. 5,107,837 (1992), and Ophir et al., U.S. Pat. No. 5,293,870 (1994). This method includes emitting ultrasonic waves along a path into the tissue and detecting an echo sequence resulting from the ultrasonic wave pulse. The tissue is then compressed (or alternatively decompressed from a compressed state) along the path and during such compression, a second pulse of ultrasonic waves is sent along the path into the tissue. The second echo sequence resulting from the second ultrasonic wave pulse is detected and then the differential displacement of selected echo segments of the first and second echo sequences are measured. A selected echo segment of the echo sequence, i.e., reflected RF signal, corresponds to a particular echo source within the tissue along the beam axis of the transducer. Time shifts in the echo segment are examined to measure compressibilities of the tissue regions.

More recently, M. O'Donnell et al., *Internal displacement and strain imaging using ultrasonic speckle tracking*. IEEE Transactions on Ultrasonic Ferroelectrics and Frequency Control; Vol. 41, 314–325, (1994), have used Fourier-based speckle tracking techniques to improve the strain measurements in the tissue produced by an external mechanical load. It has been shown that by applying incremental deformations and collecting a large set of complex B-Scan images, the strain signal-to-noise ratio can be significantly improved.

The various approaches differ both in how the medium is stressed and in how the measured ultrasound signals are processed. T. Sugimoto et al., *Tissue Hardness Measurement Using The Radiation Force of Focused Ultrasound*. IEEE 1990 Ultrasonic Symposium, 1377–80 (1990), suggested a measurement technique of hardness, where the radiation force of focused ultrasound was used to generate the deformation of the tissue, and deformation was measured as a function of time by a conventional pulse-echo technique. The radiation pressure of focused ultrasound exerts such a substantial mechanical stress in the media that even at the exposure levels typical for medical ultrasonic pulse-echo imaging devices significant acoustical streaming can be induced in a liquid. See H. C. Starritt et al., *An experimental investigation of streaming in pulsed diagnostic ultrasound beams*. Ultrasound Med Biol; Vol. 15, 363–373 (1989).

The use of radiation pressure of focused ultrasound to exert force in medium to obtain information on its mechanical properties has been described. See S. Dymling et al., *Acoustic Method For Measuring Properties of a Mobile Medium*. U.S. Pat. No. 5,056,357 (1991). They derived the information on the viscosity of the fluids by measuring the velocity of the streaming induced by radiation pressure using Doppler ultrasound.

SUMMARY OF THE INVENTION

The present invention relates to a method and to devices employing the method for Shear Wave Elasticity Imaging (SWEI) in which a shear stress is induced remotely in the tissue in the form of highly attenuating shear waves.

The core of this method is shear wave generation by radiation force of focused energy such as ultrasound from an ultrasound transducer. These remotely induced waves are detected and the tissue viscoelastic properties are evaluated from the measured propagation speed and attenuation of the shear waves. In the SWEI compared to other approaches in ultrasound elasticity imaging, the induced strain in the tissue can be extremely localized. The remotely induced shear waves are fully attenuated within a few wavelengths distance. By choosing a corresponding modulation frequency of the amplitude modulated ultrasonic pulse (typically in the low kHz range) the wavelength of shear waves is adjusted so as to minimize the influence of the boundaries on the shear wave propagation parameters. The volume of tissue involved in the mechanical excitation can be kept on the order of 1 cm$^3$ in contrast to other methods of elasticity imaging where the complete organ is subjected to shear stress. Consequently, local evaluation of viscoelastic properties is greatly simplified compared with conventional methods of elasticity imaging since trivial boundary conditions can be assumed and an infinite medium model can be used to reconstruct the mechanical properties of tissue. SWEI differs from all the other approaches in elasticity imaging as it offers the potential for measuring the local mechanical properties of tissue regions with less influence by the properties of adjacent tissue and it does not require an external deformation means or vibration source.

Great attenuation of shear waves in biological soft tissues, which is two to three orders of magnitude higher than that for the compressional waves, is the main reason that shear waves have been ignored as a possible means to obtain information on mechanical properties of tissue. Interestingly, this unfavorable feature of the high absorption of shear waves is one of the factors which makes SWEI feasible. The high attenuation of shear waves permits one skilled in the art to induce mechanical oscillations within a very limited area of tissue in the vicinity of the focal point of a focused ultrasonic beam.

One of the significant advantages of SWEI over other methods of elasticity imaging is that little additional equipment is the needed to generate shear strain in the tissue. An additional important feature of SWEI is that the parameters of the modulated ultrasonic pulse needed to induce shear waves in the tissue are such that any conventional ultrasonic imaging system potentially can be transformed into an elasticity imaging device without significant changes in its hardware.

The values of the shear modulus G and dynamic shear viscosity η of tissue are evaluated from the measured values of velocity $V_s$ and attenuation $\alpha_s$ of shear waves using the equations $$G = \frac{(R^2 - X^2)}{\rho}, \quad \eta = \frac{2RX}{\omega\rho},$$

$$V_S = \frac{R^2 + X^2}{\rho R}, \quad \text{and } \alpha = \frac{\rho\omega X}{(R^2 + X^2)},$$

where R and X are real and imaginary components of acoustic impedance of tissue, ρ is the density of the material, and ω is the angular frequency. (See L. A. Frizzell, E. L. Carstensen, and J. F. Dyro, Shear properties of mammalian tissues at low megahertz frequencies, J. Acoust. Soc. Am., Vol. 60, No. 6, 1409–1411, (1977).) There are different possibilities of ultrasonically deriving propagation parameters of shear waves needed for evaluation of tissue viscoelastic properties.

DETAILED DESCRIPTION OF THE INVENTION

Figure 1:
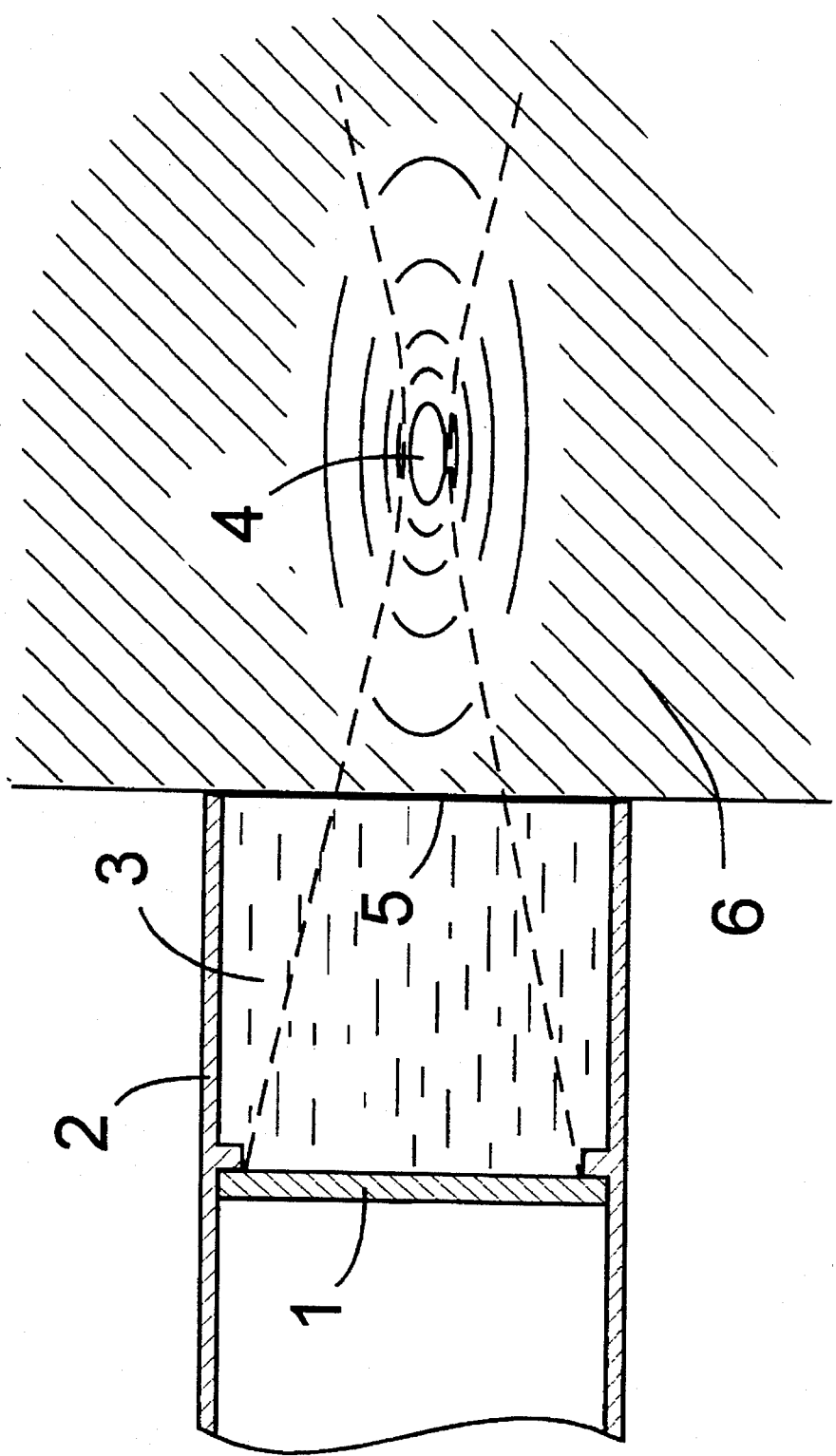
FIG. 1 shows an embodiment of the method in which a coupling liquid is used to transfer the ultrasonic wave from the transducer to the tissue. The shear wave is detected on the surface of the tissue.

The preferred embodiment of the present invention is shown in FIG. 1. The transmitting focusing transducer (1), e.g. an ultrasonic phased array or a single focused piezoceramic transducer, is enclosed in a chamber (2) filled with a coupling fluid (3). The dimensions of the chamber are such that the focal region (4) of the transducer is outside of the chamber. One wall of the chamber, and particularly the one perpendicular to the direction of the transmitting ultrasound waves, is a membrane made out of a piezoelectric polymer film (5). The membrane comes into direct contact with the examined tissue (6). Piezoelectric polymer film should satisfy a number of requirements, such as good acoustical coupling between both the fluid (3) and the tissue (6), it should be sufficiently thin and transparent to ultrasound, and most importantly, should be sensitive to mechanical oscillation in the kHz frequency range that corresponds to the frequency of the induced shear waves. All these requirements are fulfilled by using such piezomaterial as piezo polyvinylidene fluoride (PVDF) or its co-polymers manufactured by AMP, Valley Forge, Pa.

The operation of the device is as follows: The transmitting focusing transducer (1) generates an amplitude modulated ultrasonic pulse. The pulsed ultrasonic beam propagates from the transmitting transducer to the focal region (4) in the tissue (6) where it induces a shear wave corresponding to the modulating signal. This shear wave propagates through the tissue and is detected at the surface of the tissue by the receiving piezosensitive film (5). The velocity of the shear wave propagation in the tissue $c_s$ is determined from the phase shift of the transmitted and received waveform of the modulating signal, knowing the signal frequency, and the distance of the focal point of the excitation transducer from the receiving piezofilm. By measuring the amplitude of the received signal, the attenuation coefficient of the shear waves propagating in the medium $\alpha_s$ is estimated. These parameters allow for calculation of the shear viscosity η and shear elasticity modulus G. The phase and amplitude of shear waves can be obtained at different positions of the focal region by scanning the focused pulsed beam through the portion of the tissue and measuring after each pulse and, consequently, the spatial distribution of shear mechanical properties of tissue can be evaluated.

It is contemplated that for another version of the above embodiment the excitation transducer is in direct contact with the PVDF film and no coupling fluid is necessary. This version only utilizes a flat ultrasonic phased array as a transmitting focusing transducer while the embodiment shown in FIG. 1 can be realized also with a simple focused piezoceramic transducer.

Figure 2:
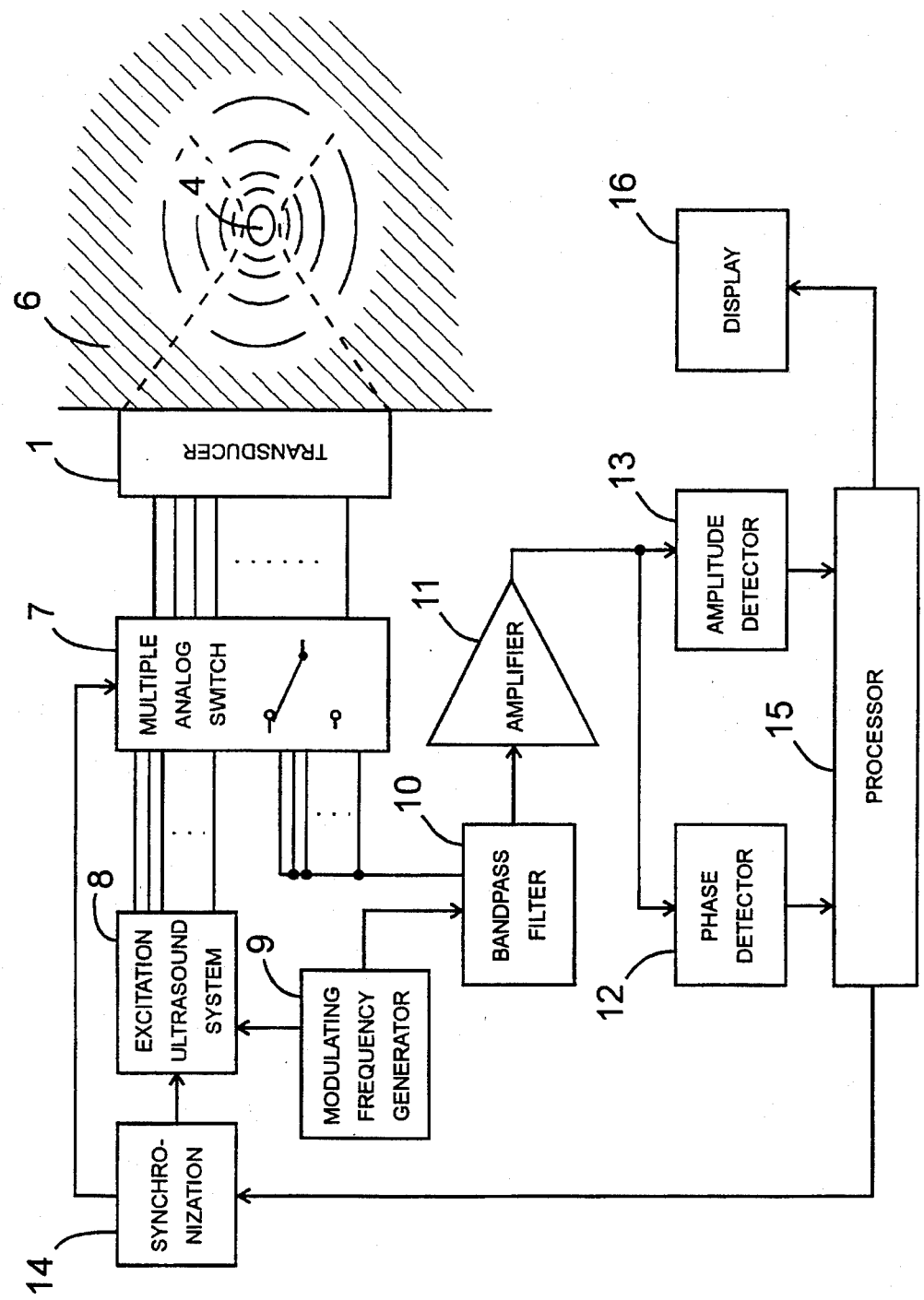
FIG. 2 shows an embodiment of the method in which an array transducer is used for both transmitting of the ultrasonic wave and detection of the shear wave at the surface of the tissue. The drawing includes a block schematic of the electronic circuitry.

Another embodiment of the present invention shown in FIG. 2 encompasses a piezoelectric phased array which is in direct contact with the tissue fulfilling both functions: transmitting excitation ultrasonic pulses and receiving low frequency shear waves. No additional piezofilm is needed. Piezomaterial used in the phased array transducer must give a flat frequency response over a very wide frequency range to fulfill efficiently both excitation and shear wave detection functions. An example of such a material is the piezoelectric composite consisting of polymer and ceramic powder mixture, the so called $d_{31}$-zero Piezo-Rubber manufactured by NGK Spark Plug Co. Ltd., Japan. See K. Ogura at al., *Wide Band Receiving Characteristics of Piezo-Rubber Hydrophone*, Japanese Journal of Applied Physics, 1992, Vol. 31 Suppl. 1, 278–280, (1992). The elements of the array (1) are time multiplexed between the ultrasonic excitation driver (8) and the shear wave receiver. After the modulated ultrasonic signal is transmitted from the phased array transducer, the driving signal is electronically disconnected, and the phased array transducer is rapidly switched to the shear wave receiving mode. An analog switch (7) is used for switching all elements simultaneously between the modes. This change of modes includes re-tuning of the phased array transducer from its resonant ultrasonic frequency (the frequency of the carrier ultrasonic excitation signal) to the lower frequency range of the shear wave. Since the shear waves are quickly decaying, the strongest signal will be received by the array element nearest to the focal point of the phased array transducer. Therefore the array form of the transducer is no longer necessary, and the shear wave can be detected from the entire array by tying all elements in parallel. The system includes synchronization circuitry (14) which controls the timing of switching and modulation.

At the end of this pulse train, the analog switch (7) ties all array elements together in parallel and connects them to the receiver. The receiver has a bandpass filter (10) at its input which is of switched capacitor type, and its center frequency is controlled by the modulating pulse generator (9). Therefore it is automatically tuned to the frequency of the generated modulating pulses and induced shear waves. The quality factor of the filter can also be programmed electronically. The filtered signal is further amplified in an amplifier (11). This signal will reflect the amplitude of the received signal and can be monitored at the output of a peak detector (13). The phase of this signal is compared with the phase of the modulating signal, and the phase shift can be determined by a phase comparator (12). The obtained data are then processed in a processor (15) and displayed on a display (16). Similar electronic filtering and detection system can be also used for the embodiment shown in FIG. 1.

It is contemplated that the propagation parameters of the shear waves induced by the radiation pressure of the amplitude modulated focused ultrasound can be detected remotely using ultrasonic pulse-echo imaging technique. The shear waves and the resulting shear strain are detected by ultrasound interrogation involving cross-correlation of sequential image data. The ultrasonic wave backscattered from the focal region of the excitation transducer contains information on the parameters of the shear waves. Since the excitation and interrogation ultrasonic waves are of the same frequency range, the same focused transducer or an array can be used for both functions: to induce shear wave and to measure its propagation properties. The modes of remote ultrasonic detection of shear waves may also include pulsed and continuous Doppler techniques.

Figure 3:
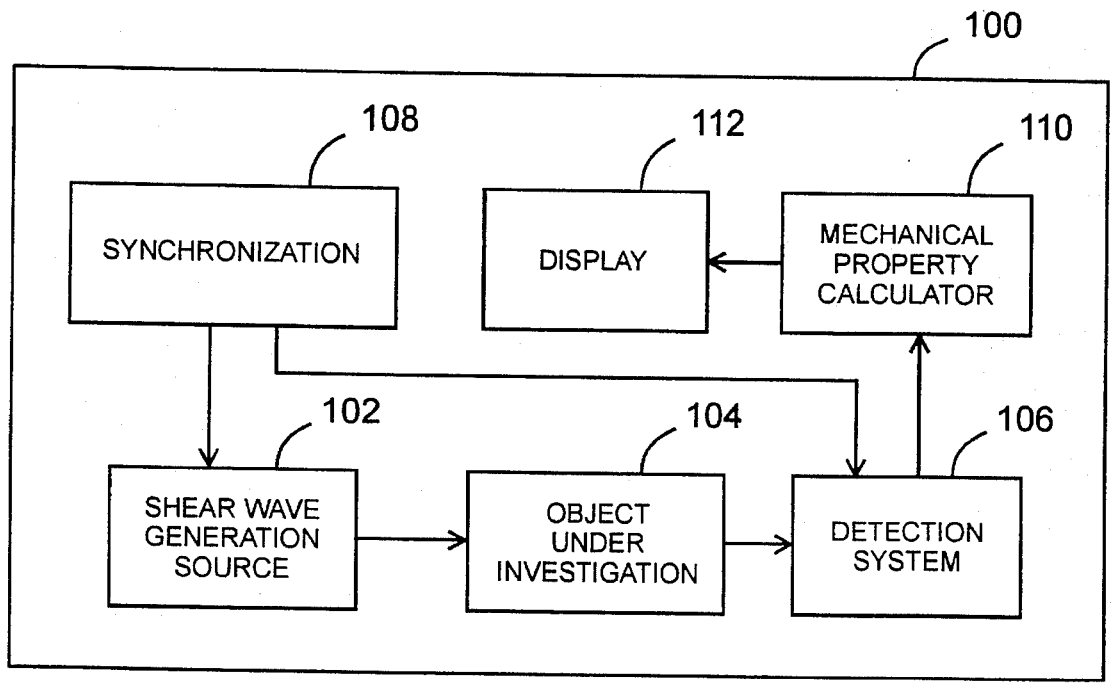
FIG. 3 shows a general schematic of the method and the device in which a remote detection of shear waves can be achieved with types of energy other than ultrasound.

FIG. 3 shows a schematic of the device in a general form, to explain a basic principle of the operation of the device and method which can be applied and other possible embodiments. The complete system designated by the numeral 100, comprises an external source of focused energy 102 that remotely generates shear waves in the investigated tissue 104. In the embodiments described above the focused energy used to induce in the tissue shear waves was amplitude modulated ultrasound but other types of focused energy interacting with tissue and inducing shear waves, such as electromagnetic waves, can be used. The detection system 106 determines at least one of the shear wave propagation parameters such as shear wave velocity, shear wave attenuation coefficient, amplitude and velocity of shear displacement of tissue particles in the propagating shear wave, spatial and temporal dependencies of these amplitude and velocity of shear displacement of tissue particles. The functioning of the shear wave generation force 102 and the detection system 106 usually need to be coordinated in time by a timing or synchronization element 108. Using the obtained data on at least one propagation parameter of shear waves the mechanical property calculator 106 evaluates at least one of the mechanical properties or tissue such as shear elasticity modulus, Young's modulus, dynamic shear viscosity, and mechanical impedance of the tissue. The calculated mechanical parameter is displayed on a display 112. The detection system 106 can employ direct detection of shear waves on the surface of the tissue, as is done in the embodiments described in FIGS. 1 and 2, or indirect remote detection of shear waves inside the tissue using different forms of radiation. Remote indirect detection of shear waves can be achieved not only with ultrasound but also using other types of energy such as electromagnetic waves and imaging techniques such as MRI. The use of MRI for detection of tissue motion in evaluating tissue elasticity is described in A. P. Sarvazyan et al, Biophysical bases of elasticity imaging, in: Acoustic Imaging, Vol.21, Ed. J. P. Jones, Plenum Press, New York, 223–240(1995) and R. Multupillair et al, Magnetic resonance elastography by direct visualization of propagating acoustic strain waves. Science Vol. 269, 1854–1857(1995).

Although certain presently preferred embodiments of the present invention have been specifically described herein, it will be apparent to those skilled in the art to which the invention pertains that variations and modifications of the various embodiments shown and described herein may be made without departing from the spirit and scope of the invention. Accordingly, it is intended that the invention be limited only to the extent required by the appended claims and the applicable rules of law.

What is claimed is:

1. A method for determining the elasticity of tissue, comprising the steps of:

(a) remotely generating shear waves in the tissue using a focused ultrasonic wave transmitted to a focal region of a focused ultrasonic source;

(b) detecting shear waves generated in the tissue;

(c) determining at least one propagation parameter of the shear waves in the tissue selected from the group of parameters consisting of shear wave velocity, shear wave attenuation coefficient, amplitude and velocity of shear displacement of tissue particles in the propagating shear wave, spatial and temporal dependencies of these amplitude and velocity of shear displacement of tissue particles; and (d) calculating, based on the results of step (c), at least one mechanical parameter of tissue selected from the group of parameters consisting of shear elasticity modulus, Young's modulus, dynamic shear viscosity, and mechanical impedance of the tissue.

2. The method of claim 1, wherein said focused ultrasonic wave is amplitude modulated for generating said shear waves.

3. The method of claim 1, wherein step (b) comprises measuring an amplitude and a phase of shear waves on the surface of the tissue.

4. A method for determining the elasticity of tissue, comprising the steps of:

(a) remotely generating shear waves in the tissue using an amplitude modulated focused ultrasonic wave;

(b) detecting shear waves generated in the tissue;

(c) determining at least one propagation parameter of the shear waves in the tissue selected from the group of parameters consisting of shear wave velocity, shear wave attenuation coefficient, amplitude and velocity of shear displacement of tissue particles in the propagating shear wave, spatial and temporal dependencies of said amplitude and velocity of shear displacement of tissue particles; and (d) calculating, based on the results of step (c), at least one mechanical parameter of tissue selected from the group of parameters consisting of shear elasticity modulus, Young's modulus, dynamic shear viscosity, and mechanical impedance of the tissue, wherein step (a) comprises the further step of focusing the amplitude modulated focused ultrasound wave at different locations in the tissue so as to generate the shear waves in the different locations in the tissue; and wherein the method comprises the further steps of:

repeating steps (b), (c) and (d) for each amplitude modulated focused ultrasound wave focused at said different locations in the tissue, and displaying the calculated values of dynamic shear viscosity and shear elasticity modulus as a function of the coordinates of said different locations in the tissue.

5. A method for determining the elasticity of tissue, comprising the steps of:
   (a) remotely generating shear waves in the tissue using an amplitude modulated focused ultrasonic wave,
   (b) detecting shear waves generated in the tissue;
   (c) determining at least one propagation parameter of the shear waves in the tissue selected from the group of parameters consisting of shear wave velocity, shear wave attenuation coefficient, amplitude and velocity of shear displacement of tissue particles in the propagating shear wave, spatial and temporal dependencies of said amplitude and velocity of shear displacement of tissue particles; and
   (d) calculating, based on the results of step (c), at least one mechanical parameter of tissue selected from the group of parameters consisting of shear elasticity modulus, Young's modulus, dynamic shear viscosity, and mechanical impedance of the tissue, wherein step (b) comprises the further steps of sending and receiving the interrogating ultrasonic waves; and step (c) includes determining shear wave propagation related parameters in at least one point of the tissue by analyzing sent and received interrogating ultrasonic waves.

6. A method for determining the elasticity of tissue, comprising the steps of:
   (a) remotely generating shear waves in the tissue using an amplitude modulated focused ultrasonic wave;
   (b) detecting shear waves generated in the tissue;
   (c) determining at least one propagation parameter of the shear waves in the tissue selected from the group of parameters consisting of shear wave velocity, shear wave attenuation coefficient, amplitude and velocity of shear displacement of tissue particles in the propagating shear wave, spatial and temporal dependencies of said amplitude and velocity of shear displacement of tissue particles; and
   (d) calculating based on the results of step (c), at least one mechanical parameter of tissue selected from the group of parameters consisting of shear elasticity modulus, Young's modulus, dynamic shear viscosity, and mechanical impedance of the tissue, wherein said amplitude modulated focused ultrasound wave comprises an ultrasound signal which is amplitude modulated with a signal having a frequency in the range 0.3 to 30 kHz.

7. A device for determining elasticity of tissue, comprising:
   transmitting means for transmitting an amplitude modulated focused ultrasound wave to a focal region of an ultrasonic source so as to induce a shear wave in the tissue;
   detecting means for detecting the shear wave induced in the tissue at said focal region;
   means for determining at least one propagation parameter of the shear waves in the tissue selected from the group of parameters consisting of shear wave velocity, shear wave attenuation coefficient, amplitude and velocity of shear displacement of tissue particles in the propagating shear wave, spatial and temporal dependencies of said amplitude and velocity of shear displacement of tissue particles; and
   calculating means for evaluating at least one mechanical parameter of the tissue selected from the group of parameters consisting of shear elasticity modulus, Young's modulus, dynamic shear viscosity, and mechanical impedance of the tissue.

8. The device of claim 7, wherein said transmitting means comprises a single element focused transmitting transducer.

9. The device of claim 7, wherein said transmitting means comprises a phased array transmitting transducer.

10. The device of claim 9, wherein said phased array transducer comprises a piezoelectric flexible composite material and is in a direct contact with the tissue.

11. The device of claim 10, wherein said means to detect shear waves is said transmitting phased array disconnected from the driving circuit generating said amplitude-modulated ultrasonic signals and connected to the receiving circuit operating at the frequency of said modulating signal.

12. The device of claim 7, wherein said detecting means is a magnetic resonance imaging device.

13. The device of claim 7, wherein said detecting means are interrogating electromagnetic waves.

14. The device of claim 7, wherein said detecting means is an interrogating ultrasonic transducer.

15. The device of claim 14, wherein said interrogating ultrasonic transducer is a part of said transmitting transducer.

16. The device of claim 14, wherein said detecting means is an interrogating ultrasonic transducer is said transmitting transducer disconnected from the driving circuit generating said amplitude-modulated ultrasonic signals and connected to the interrogating circuit.

17. The device of claim 14, wherein said interrogating ultrasonic transducer is a separate ultrasonic transducer.

18. A device for determining elasticity of tissue, comprising:
   transmitting means for transmitting an amplitude modulated focused ultrasound wave to a focal region of a focused ultrasonic source so as to induce a shear wave in the tissue;
   detecting means for detecting the shear wave induced in the tissue;
   means for determining at least one propagation parameter of the shear waves in the tissue selected from the group of parameters consisting of shear wave velocity, shear wave attenuation coefficient, amplitude and velocity of shear displacement of tissue particles in the propagating shear wave, spatial and temporal dependencies of said amplitude and velocity of shear displacement of tissue particles; and
   calculating means for evaluating at least one mechanical parameter of the tissue selected from the group of parameters consisting of shear elasticity modulus, Young's modulus, dynamic shear viscosity, and mechanical impedance of the tissue, wherein said detecting means is a piezosensitive film placed on the surface of the tissue for detecting said shear waves in the tissue.

19. The device of claim 18, wherein said transmitting means and wherein said the piezosensitive film are mounted in a probe, said piezosensitive film being separated from said transducer by a coupling liquid.

20. The device of claim 18, wherein said transmitting means and wherein said the piezosensitive film are mounted in a probe, said piezosensitive film being mounted on the surface of said transducer.

* * * * *